United States Patent
Edelson et al.

(10) Patent No.: US 6,524,855 B2
(45) Date of Patent: Feb. 25, 2003

(54) METHODS FOR INDUCING THE DIFFERENTIATION OF MONOCYTES INTO FUNCTIONAL DENDRITIC CELLS

(76) Inventors: Richard Leslie Edelson, 76 Coleytown Rd., Westport, CT (US) 06880; Carole Berger, 3935 Blackstone Ave., Riverdale, Bronx, NY (US) 10471

( * ) Notice: Subject to any disclaimer, the term of this patent is extended or adjusted under 35 U.S.C. 154(b) by 0 days.

(21) Appl. No.: 09/928,811

(22) Filed: Aug. 13, 2001

(65) Prior Publication Data

US 2002/0004044 A1 Jan. 10, 2002

Related U.S. Application Data

(62) Division of application No. 09/294,494, filed on Apr. 20, 1999.

(51) Int. Cl.[7] .............................. C12N 5/00; C12N 5/02; C12N 5/06; C12N 5/08; A01N 1/02
(52) U.S. Cl. ........................ 435/377; 435/2; 435/325; 435/347; 435/355; 435/372
(58) Field of Search .............................. 424/93.1, 93.7, 424/529, 577; 435/2, 325, 347, 366, 372, 372.1–372.3, 377, 355

(56) References Cited

U.S. PATENT DOCUMENTS

| | | | |
|---|---|---|---|
| 4,321,919 A | 3/1982 | Edelson | 128/214 |
| 4,398,906 A | 8/1983 | Edelson | 604/6 |
| 4,428,744 A | 1/1984 | Edelson | 604/6 |
| 4,464,166 A | 8/1984 | Edelson | 604/6 |
| 4,612,007 A | 9/1986 | Edelson | 604/5 |
| 4,613,322 A | 9/1986 | Edelson | 604/6 |
| 4,683,889 A | 8/1987 | Edelson | 128/395 |
| 4,684,521 A | 8/1987 | Edelson | 424/101 |
| 4,838,852 A | 6/1989 | Edelson et al. | 604/4 |
| 5,114,721 A | 5/1992 | Cohen et al. | 424/534 |
| 5,167,657 A | 12/1992 | Patel | 604/410 |
| 5,462,733 A | 10/1995 | Edelson et al. | 424/93.71 |
| 5,820,872 A * | 10/1998 | Edelson et al. | 424/277 |
| 5,849,589 A | 12/1998 | Tedder et al. | 435/377 |
| 6,010,905 A | 1/2000 | Cohen et al. | 435/372 |

FOREIGN PATENT DOCUMENTS

| | | |
|---|---|---|
| WO | WO 93/20185 | 10/1993 |
| WO | WO 94/11016 | 5/1994 |
| WO | WO 97/34472 | 9/1997 |
| WO | WO 99/38380 | 5/1999 |

OTHER PUBLICATIONS

Akagawa et al., Generation of CD1+RelB+Dendritic Cells and Tartrate–Resistant Acid Phosphatase–Positive Osteoclast–Like Multinucleated Giant From Human Monocytes, 1996; Blood,vol. 88,No. 10:4029–4039.

Edelson, Light–Activated Drugs, Scientific American, Aug. 1988, pp. 68–75.

Isolation and Function of Human Dendritic Cells by Lisa Williams, et al.; International Review of Cytology, vol. 153: 41–103, 1994.

Review of Human Dendritic Cells: Isolation and Culture from Precursors by Ron Jaffe; Pediatric Pathology 13:821–837, 1993.

Dendritic Cells: Origin and Differentiation by Ranjeny Thomas, et al., Stem Cells, vol. 14:196–206, 1996.

Article published in The Journal of Immunology, entitled – TGF–B1 Promotes In Vitro Generation of Dendritic Cells by Protecting Progenitor Cells from Apoptosis by Elisabeth Riedl, et al. vol. 158, Feb. 15, 1997, pp. 1591–1597.

Article published in The Journal of Immunology, entitled TGF–B1 Promotes In Vitro Development of Dendritic Cells from CD34+Hemopoietic Progenitors by Herbert Strobl, et al. dated Aug. 15, 1996, vol. 87, No. 7, pp. 2732–2739.

Contrasting Effects of IL–4 and CD40 Ligand on the In Vitro Differentiation of Human Dendritic Cells of Human Dendritic Cells from Cord Blood CD34[+] Hematopoietic Progenitors by B. Canque, et al., date Nov. 15, 1997, published in *Blood* vol. 90, No. 10 Supplement (Part 1 of 2), Abstract # 2123.

Abstract #668 from an article entitled: Transforming Growth Factor, etc. published in Blood by A. Garbe, et al., dated Nov. 15, 1998, vol. 92, No. 10 Supplement 1 (Part1 of 2).

flt3 Ligand in Cooperation with Transforming Growth Factor $\beta_1$ Potentiates in Vitro Development of Langerhans Type Dendritic Cells and allows Single–Cell Dendritic Cell Cluster Formation under Serurn–Free Conditions by Herbert Strobl, et al. published in *Blood*, vol. 90, No. 4, dated Aug. 15, 1997, pp. 1425–1434.

* cited by examiner

*Primary Examiner*—Dave T. Nguyen
*Assistant Examiner*—Quang Nguyen
(74) *Attorney, Agent, or Firm*—Cummings & Lockwood

(57) ABSTRACT

A method for inducing differentiation of monocytes contained in an extracorporeal quantity of a subject's blood into functional dendritic antigen presenting cells is provided. The monocytes are first treated by exposure to physical perturbation, irradiation in the presence of a photoactivatable agent capable of forming photoadducts with cellular DNA components, and/or treatment with a DNA binding agent. The treated monocytes are then incubated for a period of time sufficient to maximize the number of functional dendritic cells in the treated cell population. Functional dendritic cells generated from induced monocytes are incubated together with disease effector agents to enhance the presentation of at least one disease-causing antigen expressed by the disease effector agents.

10 Claims, 1 Drawing Sheet

METHODS FOR INDUCING THE DIFFERENTIATION OF MONOCYTES INTO FUNCTIONAL DENDRITIC CELLS

RELATED APPLICATIONS

The present application is a divisional application of patent application Ser. No. 09/294,494, filed on Apr. 20, 1999.

Field of the Invention

The present invention relates to in vivo methods for inducing the differentiation of monocytes into functional dendritic antigen presenting cells and, more particularly, to extracorporeal methods for treating and incubating monocytes to induce such differentiation. In particular, the present invention provides methods for making immunotherapeutic compositions comprising apoptotic or inactivated disease effector agents and functional dendritic cells derived from induced monocytes.

BACKGROUND OF THE INVENTION

The use of dendritic cells in cancer immunotherapy is presently an area of significant clinical inquiry. Dendritic cells are highly effective in presenting antigens to responding T-cells; however, dendritic cells normally constitute less than one percent of blood mononuclear leukocytes. Accordingly, a number of in vitro methods have been developed to expand populations of dendritic cells to augment anti-cancer immunity. By exposing increased numbers of dendritic cells to antigens on tumor or other disease-causing cells, followed by reintroduction of the antigen-loaded dendritic cells to the patient, presentation of these antigens to responding T-cells can be enhanced significantly.

For example, culturing blood mononuclear leukocytes for eight days in the presence of granulocyte-monocyte colony stimulating factor (GM-CSF) and interleukin-4 (IL-4) produces large numbers of dendritic cells. These cells can then be externally loaded with tumor-derived peptide antigens for presentation to T-cells. Alternatively, the dendritic cells can be transduced to produce and present these antigens themselves. Expanding populations of dendritic cells transduced to produce and secrete cytokines which recruit and activate other mononuclear leukocytes, including T-cells, may be an even more effective method of generating anti-tumor immune responses.

Transducing cultivated dendritic cells to produce a particular generic tumor antigen and/or additional cytokines is labor intensive and expensive. More importantly, this procedure likely fails to produce and present those multiple tumor antigens that may be most relevant to the individual's own cancer. Several approaches have been proposed to overcome this problem. Hybridization of cultivated autologous dendritic cells with tumor cells would produce tetraploid cells capable of processing and presenting multiple unknown tumor antigens. In a second proposed approach, acid elution of Class I and Class II major histocompatability complexes (MHC) from the surface of malignant cells would liberate a broad spectrum of tumor-derived peptides. These liberated peptides could then be externally loaded onto MHC complexes of autologous cultivated dendritic cells.

Conventional photopheresis is a method of vaccinating patients against leukemic lymphocytes, even when the distinctive tumor antigen(s) is not known. In this method, malignant cells are exposed to photo-activated 8-methoxypsoralen (8-MOP) which enhances cell surface display of Class I MHC-associated tumor antigens. After intravenous return of these altered malignant lymphocytes to the original patient, a potent anti-tumor response may be generated in about 25% of the patients, leading to diminution of the malignant cell population and occasionally long-standing remissions. Experimental studies in mice, in which autologous dendritic cells are first grown in tissue culture and then admixed with the 8-MOP-treated tumor cells, appears to increase the efficacy of conventional photopheresis. In this experimental protocol, tumorigenic mouse T-cells are rendered apoptotic by photopheresis using 8-MOP and exposure to ultraviolet (UV) energy. Following this chemical alteration of the malignant leukocytes, autologous cultured dendritic cells are added to the apoptotic T-cells, and the cell mix is incubated overnight with shaking to maximize contact between the T-cells and the dendritic cells. The apoptotic T-cell/dendritic cell mix has proven to be an effective cellular vaccine in test mice challenged with viable tumorigenic 2B4.11 cells.

While the above-described experimental protocol is apparently more efficient and comprehensive than alternative approaches, it requires extensive ex vivo cellular manipulations over a period of several days. Accordingly, an in vivo procedure which could in a single day provide large numbers of functional dendritic cells and expose those cells to apoptotic tumor cells would greatly simplify the means by which the anti-tumor cellular vaccine could be prepared.

SUMMARY OF THE INVENTION

The present invention is based on the convergence of two disparate phenomena: treating monocytes in a manner which induces their differentiation into functional dendritic antigen presenting cells, and treating disease effector agents to render them apoptotic or to inactivate them. By incubating these treated populations together for a period of time sufficient to optimize processing and presentation of disease associated antigens distinctive to the disease effector agents by the dendritic cells, prior to returning the dendritic antigen presenting cells to the patient, clinically enhanced immunity to the disease associated antigens is achieved.

As used herein, the term "disease effector agents" refers to agents that are central to the causation of a disease state in a subject and which express disease-associated antigens. In certain circumstances, these disease effector agents are disease-causing cells which may be circulating in the bloodstream, thereby making them readily accessible to extracorporeal manipulations and treatments. Examples of such disease-causing cells include malignant T-cells, malignant B cells, T-cells and B cells which mediate an autoimmune response, and virally or bacterially infected white blood cells which express on their surface viral or bacterial peptides or proteins. Exemplary disease categories giving rise to disease-causing cells include leukemia, lymphoma, autoimmune disease, graft versus host disease, and tissue rejection. Disease associated antigens which mediate these disease states and which are derived from disease-causing cells include peptides that bind to a MHC Class I site, a MHC Class II site, or to a heat shock protein which is involved in transporting peptides to and from MHC sites (i.e., a chaperone). Disease associated antigens also include viral or bacterial peptides which are expressed on the surface of infected white blood cells, usually in association with an MHC Class I or Class II molecule.

Other disease-causing cells include those isolated from surgically excised specimens from solid tumors, such as lung, colon, brain, kidney or skin cancers. These cells do not ordinarily circulate in the blood in significant quantity, but can be manipulated extracorporeally in analogous fashion to blood leukocytes, after they are brought into suspension or propagated in tissue culture.

In addition to disease-causing cells, disease effector agents falling within the scope of the invention further include microbes such as bacteria, fungi and viruses which express disease-associated antigens. It should be understood that viruses can be engineered to be "incomplete", i.e., produce distinguishing disease-causing antigens without being able to function as an actual infectious agent, and that such "incomplete" viruses fall within the meaning of the term "disease effector agents" as used herein.

Accordingly, the present invention provides, in one aspect, a method for inducing the differentiation of monocytes contained in an extracorporeal quantity of a subject's blood into functional dendritic antigen presenting cells. According to the invention, the monocytes are treated by at least one of the following: (1) exposing the monocytes to physical perturbation, (2) irradiating the monocytes in the presence of a photoactivatable agent capable of forming photoadducts with cellular components, and (3) treating the monocytes with a DNA binding agent. Following treatment, the monocytes are incubated for a period of time sufficient to maximize the number of functional dendritic cells.

In the preferred embodiment of this aspect of the invention, the monocytes are separated from the extracorporeal quantity of the subject's blood by leukapheresis. Following separation, the monocytes are subjected to photopheresis using 8-MOP and exposure to UV energy. The cells are then incubated for a period of from about 6 to about 48 hours, and most preferably from about 12 to about 24 hours.

The invention provides, in a second aspect, a method of enhancing the presentation of disease associated antigens. According to the method, disease effector agents contained in a quantity of a subject's blood or derived from an exogenous source and capable of expressing at least one disease associated antigen are treated to render the agents apoptotic or to inactivate them. Monocytes contained in a quantity of the subject's blood are also treated by at least one of the following: (1) exposing the monocytes to physical perturbation, (2) irradiating the monocytes in the presence of a photoactivatable agent capable of forming photoadducts with cellular components, and (3) treating the monocytes with a DNA cross-linking agent. The treated disease effector agents and the treated monocytes are then incubated together for a period of time sufficient to induce differentiation of the monocytes into functional dendritic antigen presenting cells and to optimize processing and presentation of the disease associated antigens by the dendritic cells In a preferred embodiment of this aspect of the invention, the monocytes and the disease effector agents are separated from the quantity of the patient's blood by leukapheresis. The monocytes and disease effector agents are then exposed to photo-activated 8-MOP and incubated together for a period of from about 6 to about 48 hours, and preferably for about 12 to about 24 hours. The mix is then reinfused into the subject to elicit an immune response.

DETAILED DESCRIPTION OF THE INVENTION

1. Differentiation of Monocytes

Figure 1:
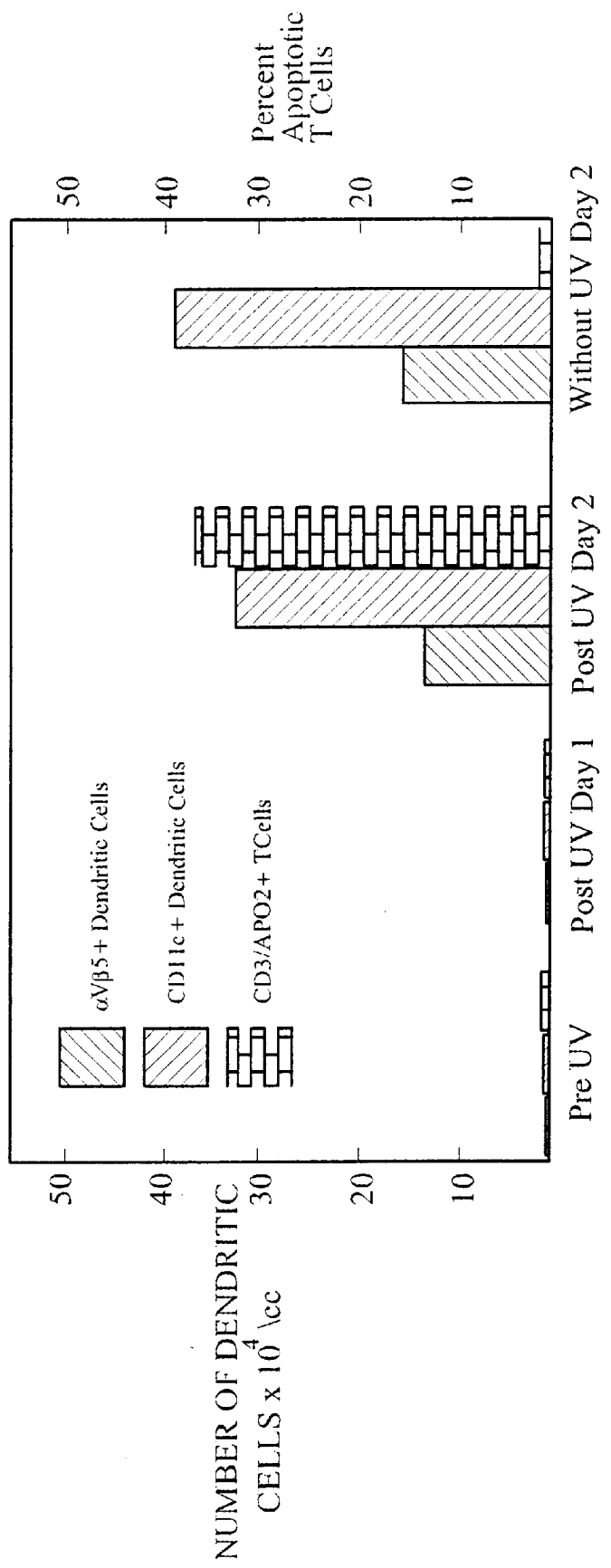
FIG. 1 is a graph which illustrates the generation of both dendritic antigen presenting cells and apoptotic T-cells following overnight incubation of blood exposed to 8-MOP and ultraviolet A energy.

As noted above, monocyte differentiation is initiated by exposing monocytes contained in an extracorporeal quantity of a subject's blood to physical perturbation, irradiation in the presence of a photoactivatable agent capable of forming photoadducts with cellular components, and/or treatment with a DNA binding agent. In the preferred embodiment of the invention, the monocytes are obtained by preparing a white blood cell concentrate in accordance with standard leukapheresis practice using a leukapheresis/photopheresis apparatus of the type well known to those skilled in the art. In addition to monocytes, the white blood cell concentrate also includes lymphocytes and some red blood cells and platelets. Typically, up to two billion white blood cells are collected during leukapheresis. Assuming that monocytes comprise from about 2% to about 50% of the total white blood cell population collected, approximately 40 million to 1 billion monocytes are present in the white blood cell concentrate.

Following separation, the monocytes are subjected to photopheresis by exposure to a photoactivatable agent which is capable of forming photoadducts with cellular components, and then irradiating the exposed cells with radiation suitable for activating the agent, typically ultraviolet or visible light. Prior to photopheresis, saline is added to the white blood concentrate to dilute the red blood cell concentration to about 2% by volume, thereby permitting more effective penetration of the activating radiation to the target leukocytes. The photoactivatable agent can be administered to the subject prior to obtaining a quantity of blood from the subject for leukapheresis and photopheresis. Alternatively, or additionally, the photoactivatable agent can be added directly to the extracorporeal bloodstream, typically by injecting the agent into the tubing leading to the leukapheresis/photopheresis apparatus. Regardless of when and how a particular agent is administered, the monocytes must be exposed to the photoactivatable agent for a period of time sufficient for the agent to enter the monocytes and react with cellular components.

Exemplary photoactivatable agents are psoralens, porphyrins, pyrenes, phthalocyanine, retinoid derivatives, photoactivated cortisone, photoactivated antibodies specifically reactive with the monocytes, photactivatable dyes, and monoclonal antibodies which have been linked to porphyrin molecules.

The psoralens are a preferred class of photoactivatable agents for use in the photopheresis procedure. Psoralens are readily absorbed from the digestive track, reaching peak levels in the blood and other tissues in one to four hours following oral administration, and these agents are excreted almost entirely within 24 hours. Accordingly, the psoralens are particularly suitable for oral administration prior to obtaining an extracorporeal quantity of the subject's blood. The psoralens molecules are inert prior to exposure to irradiation and are transiently activated to an excited state following irradiation. The transiently activated psoralens molecules are capable of forming photoadducts with cellular DNA, proteins or lipids and generating other reactive species, such as singlet oxygen, which are capable of modifying other cellular components, e.g., the cell membrane and cytoplasmic components such as proteins and aromatic amino acids.

The preferred psoralens include 8-methoxypsoralen (8-MOP), 4' aminomethyl-4, 5', 8 trimethyl-psoralen (AMT), 5-methoxypsoralen (5-MOP), and trimethyl-psoralen (TMP). 8-MOP is the most preferred photoactivatable agent for use with the methods of the invention, and the conditions for oral administration of this psoralen are described in U.S. Pat. No. 5,147,289, the disclosure of which is incorporated herein by reference.

The irradiation stage of photopheresis is performed by passing the monocyte/lymphocyte fraction through an exposure device which may be contained within the leukapheresis/photopheresis apparatus or may be physically separate. The preferred exposure device includes a transparent plastic channel having a diameter of about 1 mm disposed between opposed irradiation sources. However, it may also be a compressible transparent compartment, which can be shaken to evenly expose the suspended cells to the light. In this manner, under certain circumstances, cellular adhesion to plastic or excessive disruption of certain types of disease effector cells can be minimized. Referring again to the preferred embodiment, as the monocyte/lymphocyte fraction passes through the channel, the cells are never separated from the irradiation sources by more than about 0.5 mm of blood. Maintaining the monocytes in such close proximity to the irradiation sources has proven particularly effective in ensuring adequate exposure of the monocyte/lymphocyte fraction to the activating radiation. In the case where a psoralen such as 8-MOP is used as the photoactivatable agent, the irradiation sources emit ultraviolet A radiation (UVA) as the activating radiation. To activate the psoralen, the monocytes are typically exposed to about 1–2 joules/cm$^2$ of UVA for a period of from about 15 to about 150 minutes.

As noted above, other methods of initiating the differentiation of monocytes to functional dendritic cells may be employed. It has been found that differentiation can be initiated simply by exposing the monocytes to physical perturbation. Thus, for example, centrifuging the monocytes during leukapheresis, and/or passing the monocytes through the narrow channel in the exposure device, thereby applying gentle shearing forces to them, or subjecting the monocytes to hydrostatic pressure will initiate differentiation of the monocytes into functional dendritic cells. This differentiation into dendritic antigen presenting cells is maximized after about 6 to about 48 hours incubation, under conditions described in this application. Differentiation can also be initiated by administering a DNA binding agent, such as mitomycin C or a cis-platinum compound, to the subject. While these agents may be effective in initiating differentiation, they remain in an active state when returned to the subject and thus are not as desirable as the psoralens for treating the monocytes.

It should also be understood that it is not absolutely necessary to separate the monocytes from the extracorporeal quantity of the patient's blood prior to treatment. Subjecting the extracorporeal quantity of the patient's blood to physical forces, or administering the photoactivatable agent to the subject prior to photopheresis and/or adding the agent to the quantity of blood, and then exposing the quantity of blood including the monocytes to the activating radiation are also effective in initiating differentiation of the monocytes into functional dendritic cells. As long as the monocytes are sufficiently exposed to physical forces, and/or pharmacologic agents, such as photo-activated 8-MOP, to initiate differentiation into dendritic cells followed by subsequent incubation, separation of the monocyte population is not required.

Following treatment to initiate differentiation, the treated monocytes are sequestered for incubation. A standard blood bag may be utilized for this purpose, as is typical in photopheresis. However, it has been found to be particularly advantageous to use a blood bag of the type which does not leach substantial amounts of plasticizer and which is sufficiently porous to permit exchange of gases, particularly $CO_2$ and $O_2$. Such bags are available from, for example, the Fenwall division of Baxter Healthcare Corp. under the name Amicus™ Apheresis Kit. Various plasticizer-free blood bags are also disclosed in U.S. Pat. Nos. 5,686,768 and 5,167,657, the disclosures of which are herein incorporated by reference.

The treated monocytes are incubated for a period of time sufficient to maximize the number of functional dendritic cells in the incubated cell population. Typically, the treated monocytes are incubated for a period of from about 6 to about 48 hours, with the preferred incubation time extending over a period of from about 12 to about 24 hours. By treating monocytes in the manner described above and then incubating the treated cell population for a minimum of from about 6 to about 12 hours, and preferably from about 12 to about 40 hours, large numbers of functional dendritic cells are obtained. It has been found to be particularly advantageous to add a buffered culture medium to the blood bag and one or more cytokines, such as GM-CSF and IL-4, during the incubation period.

The mechanism by which the methods of the present invention induce monocyte differentiation into functional dendritic cells is presently under investigation. One possibility is that cytokines liberated from the treated mononuclear cells, including GM-CSF and IL-4, cause the maturation step. In the case were the monocytes are treated with 8-MOP, it may be that 8-MOP binding increases the cytoplasmic cAMP level, which is known to enhance monocyte-dendritic cell differentiation. It is also possible that other factors, either individually or collectively, have this impact, or that 8-MOP directly or indirectly through its DNA and/or protein binding has this effect. Whatever the underlying mechanism, inducing monocyte differentiation according to the invention provides dendritic cells in numbers which equal or exceed the numbers of dendritic cells that are obtained by expensive and laborious culture of leukocytes in the presence of cytokines such as GM-CSF and IL-4 for seven or more days.

The large numbers of functional dendritic cells generated during incubation provide a ready means of presenting selected disease associated antigens and are thereby conducive to efficient immunotherapy. Antigen preparations selected to elicit a particular immune response and derived from, for example, tumors, disease-causing non-malignant cells, or microbes such as bacteria, viruses and fungi, can be added directly to the blood bag during incubation. The microbes may preferably be inactivated by prior exposure to 8-MOP or other agents. It is known that 8-MOP can cause apoptosis in bacteria and fungi and can inactivate viruses. Bringing mature dendritic cells into close contact with such antigen preparations within the confines of the blood bag provides large numbers of antigen-loaded dendritic cells The antigen-loaded dendritic cells can be used as immunogens by reinfusing the cells into the subject or by otherwise administering the cells in accordance with methods known to elicit an immune response, such as subcutaneous, intradermal or intramuscular injection. As described below, it is also possible to generate antigen-loaded dendritic cells by treating and co-incubating monocytes and disease effector agents which are capable of expressing disease associated antigens.

Methods for Enhancing the Presentation of Disease Associated Antigens.

This aspect of the invention relates in general to improved immunotherapeutic methods for treating disease states mediated by disease effector agents. As discussed above, such agents comprise microbes, such as bacteria, fungi, and complete and incomplete viruses, and disease-causing clonal populations of cells, including clones of malignant cells or clones of non-malignant T- or B-cells attacking the individual's own tissues or transplanted tissues. Since these agents have distinctive antigens on their surface that permit them to be distinguished from most other cells, immune reactions can be ideally developed against their distinctive antigens. These immune reactions can then suppress or eliminate the disease effector agent populations. Through the generation of dendritic antigen-presenting cells capable of effectively introducing the relevant antigens to a responding immune system, this invention substantially enhances the likelihood of such a disease-controlling immunologic response.

Central to this aspect of the invention is the co-cultivation of increased numbers of dendritic antigen presenting cells, generated as described above, with clones of apoptotic disease-causing cells or inactivated or incomplete microbes which bear distinctive antigens. In the case of disease-causing cells, bacteria and fungi, other means of inducing apoptosis, in addition to exposure to photo-activated drugs, may be applicable.

For example, synthetic peptides with the arginine-glycine-aspartate (RGD) motif could be added to cell suspensions of the disease-causing cells isolated from the patient's blood, from excised solid tumors or tissue cultures of the same. RGD has been shown (Nature, Volume 397, pages 534–539, 1999) to induce apoptosis in tumor cells, possibly by triggering pro-capase-3 autoprocessing and activation. Similarly, apoptosis could be induced in cells having Fas receptors, by stimulating with antibodies directed against this receptor, in this way sending signals to the inside of the cell to initiate programmed cell death, in the same way that normally Fas ligand does. In addition, apoptosis can be induced by subjecting disease-causing cells to heat or cold shock, certain viral infections (i.e., influenza virus), bacterial toxins, and x-ray or gamma-irradiation. Alternatively, certain infectious agents such as influenza virus can cause apoptosis and could be used to accomplish this purpose in cell suspensions of disease-causing cells.

Hence, these approaches, although not as usually preferred as the induction of apoptosis by photo-activated 8-MOP, could accomplish the purpose of initiating apoptosis or inactivation in disease-causing cellular populations, prior to their co-cultivation with the induced dendritic antigen-presenting cells and return to the patient for purposes of immunization. Of course, it should be understood that since viruses are not cells, they cannot undergo apoptosis as that term is generally understood and used by those skilled in the art. It is known, however, that viruses can be inactivated by exposure to 8-MOP and other photo-activated drugs and therefore can be treated in this manner prior to their co-cultivation with induced dendritic antigen presenting cells.

This aspect of the invention will be described with particular reference to an enhanced therapy for treating cutaneous T-cell lymphoma. However, it should be understood that the invention is not limited to this particular application and that the invention may be employed to treat any disease state which includes as a component disease effector agents distinguishable by their own surface antigens. A number of such disease states, component effector agents and disease associated antigens have been discussed above.

Cutaneous T-cell lymphoma (CTCL) is an immune disease that is caused by a massive expansion of a single clone of aberrant T-cells. These malignant cells are distinguished by clone-specific or tumor-specific cell surface antigens, at least one set of which are derived from clone specific protein components of the clone-specific T-cell receptor. Cytotoxic T-cell responses can be generated selectively against these clone-specific antigens. During the past decade, photopheresis has become a standard immunotherapy for advanced CTCL and works, at least in part, by generating such anti-CTCL immune responses. In standard CTCL treatment using photopheresis, leukocytes and monocytes are separated by leukapheresis from an extracorporeal quantity of a subject's blood. The monocytes and leukocytes are circulated through an ultraviolet A exposure system of the type described above, in which biologically inert 8-MOP is activated to covalently bond to DNA and cytoplasmic proteins in the lymphocytes and monocytes. This is a highly directed therapy, since the drug remains active for only millionths of a second, thereby chemically altering only those cells in the exposure field and explaining the paucity of systemic side effects. Photopheresis provides increased immunogenicity of the exposed leukocytes, without causing general immunosuppression. Thus, returning the treated cells to the subject can lead to a "vaccination" effect which, in the most responsive subjects, results in a sustained immunologic response to the chemically altered and reintroduced leukocytes. Alteration and return of less than 5% of the body burden of malignant T-cells can induce a meaningful anti-tumor response which in some subjects has resulted in complete remissions lasting more than fifteen years. Methods for applying photopheresis to the treatment of CTCL are disclosed in U.S. Pat. Nos. 5,114,721 and 4,838,852 and published PCT applications WO 97/34472 and WO 94/11016, the disclosures of which are incorporated herein by reference.

The clinical results achieved through the application of photopheresis to CTCL have encouraged a search for the treatment's underlying mechanism for two major reasons. First, if the mechanism by which photopheresis vaccinates patients against their malignant cells could be better understood, it should then be possible to refine the methodology and enhance its efficacy. For example, only 25% of the patients with advanced CTCL have a major persistent response to photopheresis. While these positive responses are profound and their frequency exceeds those produced by prior conventional chemotherapy, it would be desirable to increase the efficiency of the procedure. Second, if the mechanism could be better understood, it should then also be possible to extend the revised therapy to other types of malignancies and disease processes. This application is based on the new recognition of the role of dendritic antigen presenting cells in the response to photopheresis, and more particularly on methodology of enhancing this role. Studies in experimental systems and with transformed human cells lines have yielded four lines of evidence. First, the treatment stimulates CD8 T-cells to suppress the activity of pathogenic clones of T-cells. Second, these CD8 cells, at least in CTCL where there is only a single clone of pathogenic T-cells, recognize tumor-specific peptide antigens in the context of Class I MHC complexes at the tumor cell surface. Third, exposure of human lymphoblasts to photo-activated 8-MOP triples the display of Class I complexes, peaking after overnight incubation. Finally, the treatment also causes apoptosis in lymphocytes and their ingestion by phagocytic mononuclear cells.

Multiple lines of clinical and experimental evidence have confirmed the "vaccination" phenomenon which is associated with the induction of potent CD8 responses capable of selectively suppressing aberrant T-cell populations. In the case of CTCL, at least some of the anti-cancer CD8 T-cells selectively targeted tumor-specific peptides derived from the T-cell receptor proteins of the malignant cells. Since the T-cell receptors of CD8 T-cells recognize antigenic peptides in the context of Class I MHC, attention has focused on the impact of 8-MOP on the display of these complexes. It has recently been reported that 8-MOP triples the display of Class I at the cell surface of transformed human lymphocytes, maximizing about 22 hours after exposure, and that this effect is dependent on the degradation of cytoplasmic proteins and the transport of the generated peptide fragments across the endoplasmic reticulum through TAP pores. This effect appears to be initiated by binding of 8-MOP to aromatic amino acids of cytosolic proteins rather than the drug's other main molecular target, pyrimidine bases of DNA.

The present invention is based on the assumption that if an immune response is to be generated against weakly immunogenic complexes containing the relevant antigens, then such a response might be maximized if the complexes are maximized on the antigen presenting cells. In conventional photopheresis, T-cells are immediately returned to the subject at a point when apoptosis is only modestly elevated over baseline and when Class I complexes are also only modestly enhanced. In the present method, the treated leukocytes are incubated overnight, typically for a period of from about 6 to 48 hours. An unexpected finding was that overnight incubation of the treated cells not only enhances the expression of Class I complexes by the apoptotic T-cells, but also maximized the maturation of monocytes into functional dendritic cells. Thus, the convergence of these two phenomena made the incubation phase a simple means of bringing large numbers of apoptotic malignant cells into apposition with increased numbers of functional dendritic cells capable of ingesting apoptotic cells or fragments of apoptotic cells. It has previously been shown the mononuclear cells in the photopheresis bag have already begun to phagocytose apoptotic T-cells, although these mononuclear cells do not have the properties of dendritic cells. Typically, antigen presenting cells process endocytosed antigens through the Class II MHC pathway, which ordinarily stimulates expression of CD4 T-cells rather than the desired CD8 cytoxic cells which "see" antigens only in the context of Class I MHC. However, it is important to note that it has recently been reported that dendritic cells have a special capacity to process and present antigens derived from apoptotic cells through the Class I MHC system.

An enhanced photopheresis protocol based on the present invention has provided encouraging clinical results in a pilot study which included four subjects suffering from advanced CTCL. However, before discussing the clinical results of the study, a treatment protocol embodying the present invention will be set forth in the following examples.

EXAMPLE I

Photopheresis Protocol

The first step, which is the photopheresis protocol, is essentially the same as the protocols currently approved by the FDA. Subjects receive either oral 8-MOP (0.6 mg/kg) or intravenous 8-MOP directly into the photopheresis apparatus, to yield a concentration of 50–200 ng/ml of drug. Next, the blood is leukapheresed to obtain a buffy coat and is then passed through a contiguous closed circuit ultraviolet A exposure device, which delivers about 1–2 joules /$cm^2$ of ultraviolet A energy (320 nm–400 nm). In this manner, about 1 to 100 molecules of 8-MOP are induced to covalently bind to each million base pairs of DNA. A nearly equal amount of 8-MOP is induced to covalently bind to aromatic amino acids of cytoplasmic proteins. The treated leukocyte fraction, comprising a total volume of approximately 250 cc, is combined with 500 cc saline and then sequestered in a standard blood bank bag, as is typical for the photopheresis procedure. Following photopheresis, the treated fraction is subjected to the following novel incubation phase protocol.

EXAMPLE II

Incubation Phase Protocol

Following collection of the post photopheresis sample after ultraviolet A activation with 8-MOP, the treated cell populations are incubated as follows:

1. Remove two Amicus platelet storage bags (Baxter Fenwall PL 2410) from an apheresis kit (Baxter Fenwall 4R 23-12) by heat sealing the tubing and cutting the tubing at the end connecting to the kit.

2. Insert a sharp catheter into the pheresis bag (spike), thereby breaking the seal, with a Charter Medical 3-leg transfer set (#O3-220-02) and clamp the tubing. Spike the two Amicus bags with the other piercing pins of the same transfer set thereby establishing a passageway for the transfer of the cell suspension.

3. Hang the pheresis bag on an IV pole and open the clamp allowing ½ of the pheresis to drain into each Amicus bag by gravity, and then clamp the tubing.

4. Remove the spikes and replace with sampling site couplers.

5. Place each Amicus bag in a separate Fenwall centrifuge bag and into a centrifuge carrier.

6. Centrifuge for 10 minutes, at 1000 rpm, 23° C., to concentrate the cells as a pellet at the bottom of each bag to permit removal of a large fraction of the plasma, which contains traces of plasticizer.

7. After centrifugation, insert a needle attached to the tubing on a transfer pak into the e sampling coupler on one of the Amincus bags.

8. Carefully place the Amicus bag in a plasma extractor to avoid resuspending the cell pellet. Close the extractor and express the plasma into the transfer bag by slowly tipping the extractor forward. When approximately 50 cc has drained into the transfer bag and/or the pellet begins to resuspend, return the extractor to an upright position and remove the needle.

9. Remix the contents of the bags by gentle agitation being careful to resuspend any adherent cells attached to the bag wall.

10. Spike one 500 cc bottle containing 100 cc of colorless RPMI 1640 media with Hepes Buffer with a Baxter vented medication set and clamp the tubing. Insert the attached needle into the sampling coupler port on the first Amicus bag. Hang the bottle on the IV pole and open the tubing allowing the media to drain into the bag.

11. Clamp the tubing and remove the needle and discard the medication set. Mix the bag by gentle inversion and place the bag in a 370_C incubator on a shelf with the Abel side down, overnight.

12. Repeat steps 8–12 for the second bag.

13. Following incubation for a period of about 6 to about 24 hours, remove one bag from the incubator, gently mix by agitation and inversion, making sure that all adherent cells are resuspended. Take out 60 cc of blood in a syringe. Inject one aerobic, and one anaerobic blood culture bottle for microbiology. Inject one lavender top tube for WBC and differential to be sent to hematology.

14. Resuspend the second Amicus bag and place both bags in individual centrifuge bags and centrifuge.

15. Remove and transfer the supernatant fluid as described in steps 8–10.

16. Return well mixed blood to the patient.

FIG. 1 is a composite graph which illustrates the generation of both dendritic antigen presenting cells and apoptotic T-cells following treatment by the photopheresis and incubation protocols set forth above. As shown in FIG. 1, pre-treatment blood contained nearly undetectable numbers of dendritic cells, using either the $\alpha V\beta 5$ or CD11c markers for identification. After incubation for about 22 hours, both of these markers revealed large numbers of mature dendritic cells. Similarly, the pre-treated blood contained very few apoptotic T-cells. Only after overnight incubation did apoptotic T-cells become significantly evident, as illustrated by the simultaneous identification of the T-cells with the CD3 marker and the apoptotic cells with the APO2 markers.

The fourth set of bars at the far right of the graph illustrates the differentiation of monocyte into mature dendritic cell by means of physical perturbation and incubation only, without exposure to ultraviolet light. Differentiation was initiated by isolating monocytes and T-cells from an extracorporeal quantity of blood by leukapheresis. The isolated monocytes and T-cells were not subjected to photopheresis but were exposed only to the centrifugal forces associated with leukapheresis. The isolated cell populations were then incubated for a period of about 22 hours according to the incubation protocol set forth above. As shown in FIG. 1, the physical forces applied during leukapheresis, together with overnight incubation, caused the monocytes to efficiently evolve into functional dendritic cells, as identified by the $\alpha V\beta 5$ and CD11c markers. No significant apoptosis of the T-cells was observed, indicating that treatment with 8-MOP followed by exposure to UV, or some other form of treatment as described above, is required to induce T-cell apoptosis.

The Y axis of the graph gives the number of functional dendritic cells per cubic centimeter. Since the total volume incubated over the 22 hour period was 250 cc, 32.5 million dendritic cells (130,000×250) were generated, as indicated in the third set of bars by the CD11c marker. It has been shown that dendritic cells having this level of maturity phagocytose apoptotic cells and are efficient presenters of antigens derived from such cells. Monocytes may also ingest apoptotic cells or fragments of such cells, but monocytes cannot efficiently present antigen material processed from the apoptotic cells to CD8 cytoxic T cells. CD8 T cells only recognize antigens which are associated with Class I MHC at the surface of the antigen presenting cell. Monocytes primarily present antigens derived from ingested cells in association with Class II MHC molecules, which CD8 T cells cannot recognize. Dendritic cells, on the other hand, in part because they include the $\alpha V\beta 5$ integrin, have the special ability to "cross-prime" CD8 T cells by presenting the antigens derived from the digestion of apoptotic cells and displaying the processed antigens in association with the Class I MHC molecules that CD8 cytoxic T cells can recognize. This is a major reason why functional dendritic cells are so useful in stimulating tumor immunity, or suppressing undesirable immunologic processes by attacking the aberrant T cells that cause them.

The graph illustrated in FIG. 1 further demonstrates an effective means of determining the optimum incubation time for the mixed cell populations. Since the particular markers employed permit the numbers of dendritic cells and apoptotic T-cells to be quantified simultaneously, the incubation time that results in the optimal combination of apoptotic cells and newly formed dendritic cells can be readily determined. This is the controlling determinant establishing when to terminate incubation and reinfuse the incubated cells into the subject.

As noted previously, an incubation time of from about 12 to about 48 hours results in a maximum number of dendritic cells. The apoptotic T-cells maximize in a period of about 6 to about 40 hours. Accordingly, an incubation period of from about 6 to about 24 hours provides the most advantageous combination of apoptotic T-cells and dendritic cells. After an incubation period of this duration, the number of apoptotic cells is at a maximum and large numbers of functional dendritic cells are also present in the incubation bag. Thus, a maximum number of apoptotic cells capable of expressing disease-associated antigens are present and a large number of functional dendritic cells capable of processing and presenting those antigens are also present. In the case where the disease effector agent is derived from an exogenous source and is added to the incubation bag, the incubation period required for maximizing the number of apoptotic cells is obviously not a factor. In such instances, the time period required for maximizing the number of induced dendritic cells is the factor which determines the duration of the co-incubation.

Clinical Efficacy of Combined Treatment and Co-Incubation

The treatment method taught by the present invention has been tested in a pilot study involving four CTCL subjects whose disease had been advancing while on standard photopheresis. The four patients in the pilot study were carefully selected from a large CTCL population based on three criteria: (1) increasing tumor burden despite continued conventional photopheresis; (2) malignant clones that could be quantified in blood; and (3) low absolute blood CD8 levels. The leukemic cells in three of the subjects could readily be distinguished from normal T-cells, since their clonal T-cell receptor phenotype was recognizable using fluorescein-tagged anti-family V T-cell receptor monoclonal antibodies (V mAb). Values above 5% indicate expansion of the malignant clone. Although the clonal T-cell receptor of the fourth patient's CTCL cells does not bind any currently available V mAb, the CD4/CD8 ratio permits quantitation of that patient's leukemic population as well. The unresponsiveness of the four patients to conventional photopheresis likely reflects their CD8 T cell deficiency, since clinical responders usually require an intact CD8 compartment. Therefore, these patients present a significant challenge for the new treatment approach. Although the study population was small, it was easy to quantify reversal of disease progression in this poor prognosis patient group.

Following treatment with the above-described protocoantil, each of the four patients had a diminution in the absolute circulating malignant pool over the twelve months of the protocol. Whereas none experienced complete hematologic remission, the previous rapid increases in blood CTCL cells were reversed. Those symptomatic infections common in individuals whose immune systems have been compromised by their CTCL, and the therapy for this disease, were not encountered. Measurements of tumor burden and clinical response centered on blood determinations and quantitation of the number of infiltrating T cells in biopsies of the clinically most severe skin lesions. It is important to note that the severity and distribution of skin lesions in three of the four patients lessened. In one patient, long-standing, maximal, generalized exfoliative erythroderma associated with intractable pruritus was transformed to low grade, nearly asymptomatic erythroderma, and two of the other patients had nearly complete cutaneous remissions.

The photopheresis/incubation protocol tested in this study, like conventional photopheresis, appears to be safe, since no side effects were encountered in these subjects. Further, the capacity of the protocol to bring together malignant apoptotic cells bearing the relevant immunizing antigens with functional dendritic cells capable of presenting these antigens to a responding immune system offers additional opportunities for immunotherapy beyond the treatment of CTCL. For example, in a recently reported randomized, controlled trial, the combination of photopheresis with conventional immunosuppressive drugs proved effective in reducing the number of rejection episodes experienced by heart transplant recipients. Preliminary, studies have also suggested the efficacy of conventional photopheresis in certain autoimmune diseases, such as rheumatoid and psoriatic arthritis, lupus erythematosus, scleroderma and graft-versus-host disease (following allogeneic bone marrow transplantation). The present invention's capacity to provide an in vivo source of large numbers of dendritic cells should enhance these therapies. Modifications to the protocol may also permit co-cultivation of dendritic cells derived from induced monocytes with suspended apoptotic solid tumor cells, apoptotic infectious microbes or inactivated or incomplete viruses.

Accordingly, it should be understood, as noted above, that while certain aspects of the invention has been described in connection with an enhanced therapy for CTCL, the invention is applicable to a broad range of immune diseases without departing from the spirit and scope of the invention.

We claim:

1. A method for inducing differentiation of monocytes contained in an extracorporeal quantity of a mammal's blood into functional dendritic antigen presenting cells, said method comprising the steps of:

(a) treating the monocytes by pumping the monocytes contained in the extracorporeal quantity of blood through a plastic channel at a suitable flow rate to apply a shearing force to the monocytes; and (b) incubating the treated monocytes for a period of time sufficient to allow formation of functional dendritic cells from the treated monocytes.

2. The method of claim 1, wherein prior to step (a) the method further comprises the step of:

separating the monocytes from the extracorporeal quantity of the subject's blood by subjecting the quantity of blood to a leukapheresis process.

3. The method of claim 2, wherein the monocytes are incubated for a period of from about 6 to about 48 hours.

4. The method of claim 3, wherein the monocytes are incubated for a period of from about 12 to about 24 hours.

5. The method of claim 3, wherein the treated monocytes are incubated together with at least one of GM-CSF or IL-4.

6. The method of claim 3, wherein the monocytes are incubated in a container which does not leach substantial amounts of plasticizer and which is sufficiently porous to permit exchange of gases.

7. The method of claim 3, wherein the treated monocytes are incubated together with at least one selected antigen to be processed and presented by the dendritic cells.

8. The method of claim 7, wherein the at least one antigen is expressed on the surface of a disease effector agent.

9. The method of claim 8, wherein the disease effector agent is selected from the group consisting of disease-causing cells and microbes.

10. The method of claim 1, wherein the plastic channel is contained in a photopheresis apparatus.

* * * * *